(12) United States Patent
John

(10) Patent No.: US 9,615,797 B2
(45) Date of Patent: Apr. 11, 2017

(54) METHOD, APPARATUS AND SYSTEM FOR DETERMINING A HEALTH RISK USING A WEARABLE HOUSING FOR SENSORS

(71) Applicant: Jaison C John, Houston, TX (US)

(72) Inventor: Jaison C John, Houston, TX (US)

(73) Assignee: Jaison C. John, Missouri City, TX (US)

( * ) Notice: Subject to any disclaimer, the term of this patent is extended or adjusted under 35 U.S.C. 154(b) by 0 days.

(21) Appl. No.: 14/215,024

(22) Filed: Mar. 17, 2014

(65) Prior Publication Data

US 2014/0266752 A1    Sep. 18, 2014

Related U.S. Application Data

(60) Provisional application No. 61/802,403, filed on Mar. 16, 2013.

(51) Int. Cl.
| | | |
|---|---|---|
| G08B 21/00 | (2006.01) | |
| A61B 5/00 | (2006.01) | |
| A61B 5/11 | (2006.01) | |
| G08B 21/04 | (2006.01) | |
| A61N 1/04 | (2006.01) | |
| A61N 1/36 | (2006.01) | |

(52) U.S. Cl.
CPC .......... *A61B 5/7275* (2013.01); *A61B 5/1117* (2013.01); *A61B 5/6803* (2013.01); *A61N 1/0468* (2013.01); *A61N 1/0476* (2013.01); *A61N 1/36014* (2013.01); *G08B 21/0461* (2013.01)

(58) Field of Classification Search
CPC .. A61B 5/7275; A61B 5/6803; A61N 1/0468; A61N 1/0476
See application file for complete search history.

(56) References Cited

U.S. PATENT DOCUMENTS

| | | | | |
|---|---|---|---|---|
| 5,287,562 A | * | 2/1994 | Rush, III | A41D 13/018 2/413 |
| 5,546,609 A | * | 8/1996 | Rush, III | A41D 13/018 2/413 |
| 6,154,889 A | * | 12/2000 | Moore, III | A42B 3/324 2/411 |
| 6,560,789 B2 | * | 5/2003 | Whalen | A42B 3/122 2/413 |
| 6,826,509 B2 | * | 11/2004 | Crisco, III | A42B 3/046 2/422 |

(Continued)

*Primary Examiner* — Joseph Feild
*Assistant Examiner* — Rufus Point
(74) *Attorney, Agent, or Firm* — Jaison C. John

(57) ABSTRACT

In some embodiments, a method, apparatus, and a system for sensing a force are provided. The apparatus may comprise a plurality of sensors configured to detect an impact force. The plurality of sensors may be arranged into a housing, such as a sports helmet. The apparatus also includes a controller operatively coupled to the plurality of sensors. The controller is adapted to: receive a signal from at least one of the plurality of sensors; determine whether a value of the signal exceeds a threshold; perform a responsive action in response to a determination that the value of signal exceeds the threshold. The responsive action comprises providing a warning, performing a logging function, and/or performing a counteraction.

19 Claims, 11 Drawing Sheets

(56) References Cited

U.S. PATENT DOCUMENTS

| | | | | |
|---|---|---|---|---|
| 8,127,373 B1* | 3/2012 | Fodemski | ............. | A42B 3/046 2/410 |
| 8,265,730 B2* | 9/2012 | Alexander | ............ | A61B 5/1114 600/410 |
| 8,947,195 B1* | 2/2015 | Anvari | .................. | G05B 13/02 340/3.1 |
| 8,981,952 B2* | 3/2015 | Howard | ................ | A42B 3/046 2/10 |
| 9,007,217 B1* | 4/2015 | Anvari | .................. | H04B 1/385 340/540 |
| 9,132,271 B2* | 9/2015 | Kolen | ................. | A61N 1/0456 |
| 2002/0060633 A1* | 5/2002 | Crisco, III | ............ | A42B 3/046 340/669 |
| 2005/0266967 A1* | 12/2005 | Considine | ............. | A63B 69/20 482/84 |
| 2010/0005571 A1* | 1/2010 | Moss | .................... | A42B 3/046 2/410 |
| 2011/0246123 A1* | 10/2011 | DelloStritto | ............ | A61B 5/11 702/141 |
| 2012/0102630 A1* | 5/2012 | Anderson | ........... | A42B 3/0486 2/413 |
| 2012/0191397 A1* | 7/2012 | Eatwell | ................... | A61B 5/11 702/94 |
| 2012/0304365 A1* | 12/2012 | Howard | ................ | A42B 3/046 2/410 |
| 2014/0000011 A1* | 1/2014 | Johnson | ................ | A42B 3/046 2/413 |
| 2014/0101830 A1* | 4/2014 | Shapiro | ................. | A42B 3/285 2/414 |
| 2016/0148531 A1* | 5/2016 | Bleich | ................ | A61B 5/0205 434/247 |

* cited by examiner

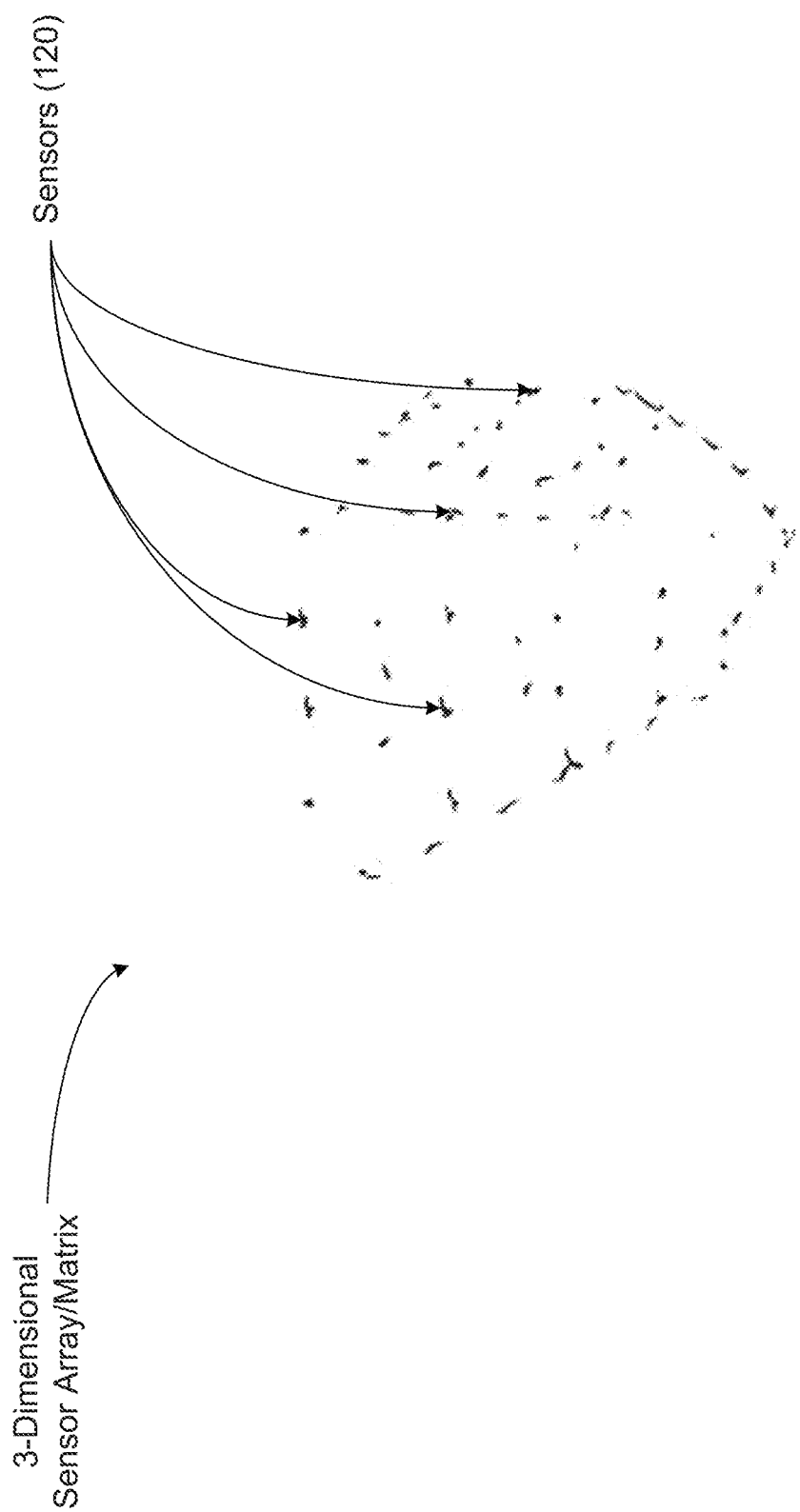

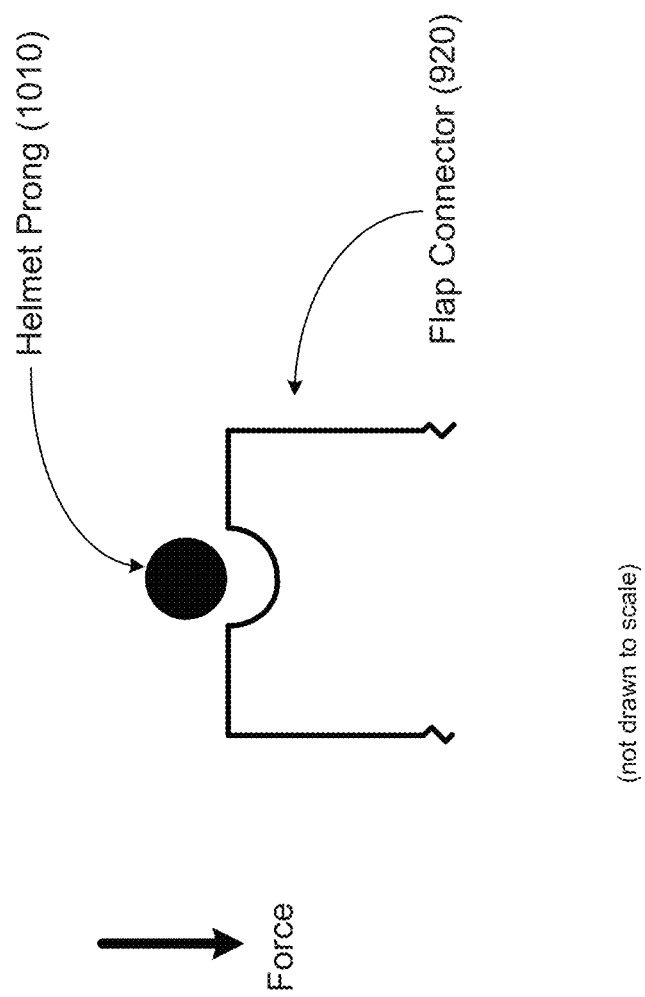

METHOD, APPARATUS AND SYSTEM FOR DETERMINING A HEALTH RISK USING A WEARABLE HOUSING FOR SENSORS

CROSS-REFERENCE TO RELATED APPLICATION

The present application claims the benefit under 35 U.S.C. §119(e) of provisional application 61/802,403, filed Mar. 16, 2013, the disclosure of which is hereby incorporated by reference herein.

FIELD OF THE DISCLOSURE

This disclosure relates to determining health risks, and more specifically to a method, apparatus, and system for determining a health risk and providing using a wearable housing, such as a helmet, for sensors.

BACKGROUND

There have been many advancements in the area of wearable protection systems, such as helmets. Most of the advancements have been focused improvement of the materials for protecting against impact forces. A few designers have attempted to implement some electronics into helmets. However, these attempts fail to provide robust information with regard to detection and/or warning of health risks. The state-of-the-art lacks an efficient and innovative means for providing sufficient complex information regarding detection, assessing, predicting, and/or analyzing health risks based upon circumstances surrounding a person using wearable protection systems.

The present disclosure is directed to addressing and/or at least reducing one or more of the problems or issues identified above.

SUMMARY OF THE DISCLOSURE

In some embodiments, a method is provided for determining a health risk using a wearable housing. A sensor array comprising a plurality of sensors detects a kinetic signal. A kinetic index is determined based upon the kinetic signal. A determination is made as to whether the kinetic index is indicative of an impact force that is above a predetermined threshold. A responsive action is performed as a result. The responsive action includes at least one of providing a warning, logging data associated with the impact force, and/or performing a counteraction.

In other embodiments, an apparatus determining a health risk using a wearable housing is provided. The apparatus may comprise plurality of sensors configured to detect a kinetic signal. The plurality of sensors is arranged into a wearable housing. The apparatus also comprises a controller operatively coupled to the plurality of sensors. The controller is configured to: receive a kinetic signal from at least one of the plurality of sensors; determine whether a directional component, a magnitude component, a location component, or a duration component of the kinetic signal respectively exceeds a corresponding directional threshold, a magnitude threshold, a location threshold, or a duration threshold; and perform a responsive action in response to a determination that at least one of the directional component, the magnitude component, the location component, or the duration component of the kinetic signal exceeds a corresponding directional threshold, magnitude threshold, location threshold, or the duration threshold. The responsive action comprises at least one of providing a warning, logging data associated with the impact force, and/or performing a counteraction.

In some embodiments, a system for determining a health risk using a wearable housing is provided. The system comprises a housing. The housing comprises a plurality of sensors configured to detect configured to detect signals, e.g., body signals, kinetic signals, etc. The plurality of sensors is arranged into the housing. The housing also comprises a controller operatively coupled to the plurality of sensors. The controller is configured to: receive a signal from at least one of the plurality of sensors; determine a kinetic index based upon the signal; determine whether there is a health risk based upon the kinetic index; and perform a responsive action in response to the health risk. The responsive action comprises at least one of providing a warning, logging data associated with the health risk, and/or performing a counteraction. The system also comprises a base station operatively coupled to the housing. The base station is adapted to receive the warning and/or log the data associated with the health risk.

BRIEF DESCRIPTION OF THE DRAWINGS

The disclosure may be understood by reference to the following description taken in conjunction with the accompanying drawings, in which like reference numerals identify like elements, and in which:

FIGS. 6A and 6B show a stylized depiction of a 3-dimensional array of sensors, in accordance with some embodiments.

FIG. 10 shows a stylized depiction flap connector of FIG. 8, in accordance in accordance with some embodiments.

Figure 1:
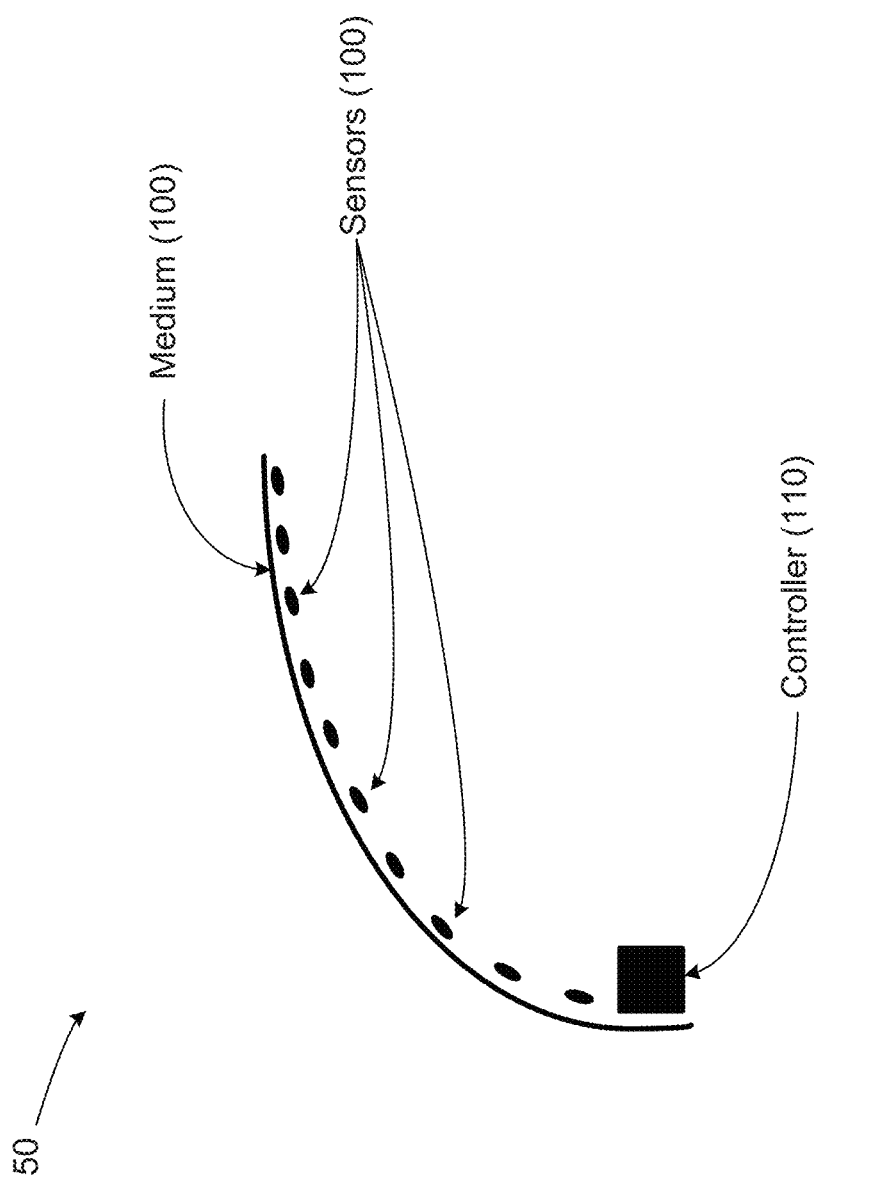
FIG. 1 shows a stylized side view depiction of an array of sensors, in accordance with some embodiments.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

DETAILED DESCRIPTION OF SPECIFIC EMBODIMENTS

Illustrative embodiments of the disclosure are described herein. For clarity, not all features of an actual implementation are described. In the development of any actual embodiment, numerous implementation-specific decisions must be made to achieve design-specific goals, which will vary from one implementation to another. Such a development effort, while possibly complex and time-consuming, would nevertheless be a routine undertaking for persons of ordinary skill in the art having the benefit of this disclosure.

Embodiments disclosed herein provide for one or more sensors that may be positioned into a housing such as a helmet, or on an apparel of a person, e.g., a space suit, clothing, sports uniforms, workout apparel, etc. Data from the one or more sensors may be used to determine whether a kinetic event of sufficient magnitude has taken place. If a determination is made that a kinetic event has taken place, a responsive action may be taken. The responsive action may include providing a warning of a health event or risk (e.g., occurrence of a concussion or risk of a concussion), logging pertinent data surrounding the circumstances of the health event or risk, and/or performing a counteraction (e.g., providing a therapeutic electrical signal, counteracting an impact force in real time or near real time, etc.).

In one embodiment, a plurality of sensors organized in a matrix for example, and arranged onto clothing, object, and/or a housing, such as a helmet. The sensors may provide cardiac, respiratory, and/or neurological data. The sensor may provide kinetic data experienced by a person's body. The acquired data may be processed to determine if an injury has occurred or whether a risk or probability of an injury exists. Based upon these determinations, a responsive action may be taken, such as providing a warning, providing an assessment of a health risk, logging data associated with the injury, and/or providing a therapy. In alternative embodiments, a single sensor may be used to acquire data and determine risk of injury.

Turning now to FIG. 1, a stylized side view depiction of one an array of sensors, in accordance with some embodiments, is illustrated. An array of sensors (e.g., accelerometers) 120 maybe placed as an array in a flexible material/medium 100. In other embodiments, the sensors 120 may be other body sensors that may be capable of sensing various body signals of a person. The sensors 120 may be capable of sensing body signals, such as cardiac signals, neurological signals, respiratory signals, etc. In some embodiments, the sensors 120 may reside within a wearable structure, such as a helmet, a padding (knee pad), a brace (e.g., knee brace), a clothing item, a belt, etc. each comprising electronics, to process the signals and provide for communications. In other embodiments, the sensors 120 may reside external to the wearable structure, wherein the wearable structure may comprise circuitry to process the signals and facilitate communications (wired or wireless) between the sensors and the wearable structure.

In some embodiments, the sensors 120 may comprise one or more kinetic sensors that are capable of detecting a variety of type of kinetic signals. The sensor 120 may be an accelerometer, an inclinometer, a gyroscope meter, and/or any type of sensor capable of detecting movement or force. In an alternative embodiment, a single sensor may be used. In one embodiment, a single sensor 120 may be placed on a medium 100. In other embodiments a plurality of sensors 120 may be positioned on the medium 100. The medium 100 may be of various types of materials, e.g., a foam material, a gel-type material, other natural and/or chemically derived materials, etc. The sensors 120 may be interconnected by wired connection, or by wireless (e.g., radio-frequency (RF), microwave, Bluetooth, cellular communication, Wi-Fi, etc.) connections. In other embodiments, each sensor 120 may be separately connected to another device, such as a controller 110. One or more of the set of sensors 120 ("sensor set") being affixed to the medium 100 may be configured as electrodes, which could be placed in a variety of locations, e.g., inside a sports helmet. In some embodiments, one or more sensors 120 may reside in the facemask or other portions of a sports helmet.

The sensors 120 may be operatively coupled to the controller 110. In one embodiment, the controller 110 may also be affixed to the medium 100. The sensors 120 may be in communication with the controller 110 using wired or wireless connections. The controller 110 is capable of controlling operations of the sensors 120. Signals sensed by the sensors 120 may be processed by the controller 110. Moreover, various responsive actions may be taken by the controller 110, including providing a warning, logging a sensed event (e.g., a high impact event, occurrence of a risk of health, etc.), including a location of the event, direction of the impact, etc.), and/or providing a therapeutic electrical signals.

The medium 100, the sensor(s) 120, and the controller 110 may be part of a medium assembly 50. In one embodiment, a housing (e.g., helmet) may be designed to house the medium assembly 50. The housing may comprise a one or more output devices that may provide a message regarding a health risk determined by the controller 110. The output device may comprise a visual output device (e.g., an LED display), an audio output device (e.g., a speaker), and/or a mechanical output device (e.g., a vibration output device). The output devices may be activated by the warning unit 280. In other embodiments, the medium assembly 50 (including the medium 100, the sensor(s) 120, the controller 110) may be housed in a knee brace, an elbow brace, an ankle brace, a wrist brace, an apparel, such as a T-shirt, shorts, etc., shoes, etc.

Figure 2:
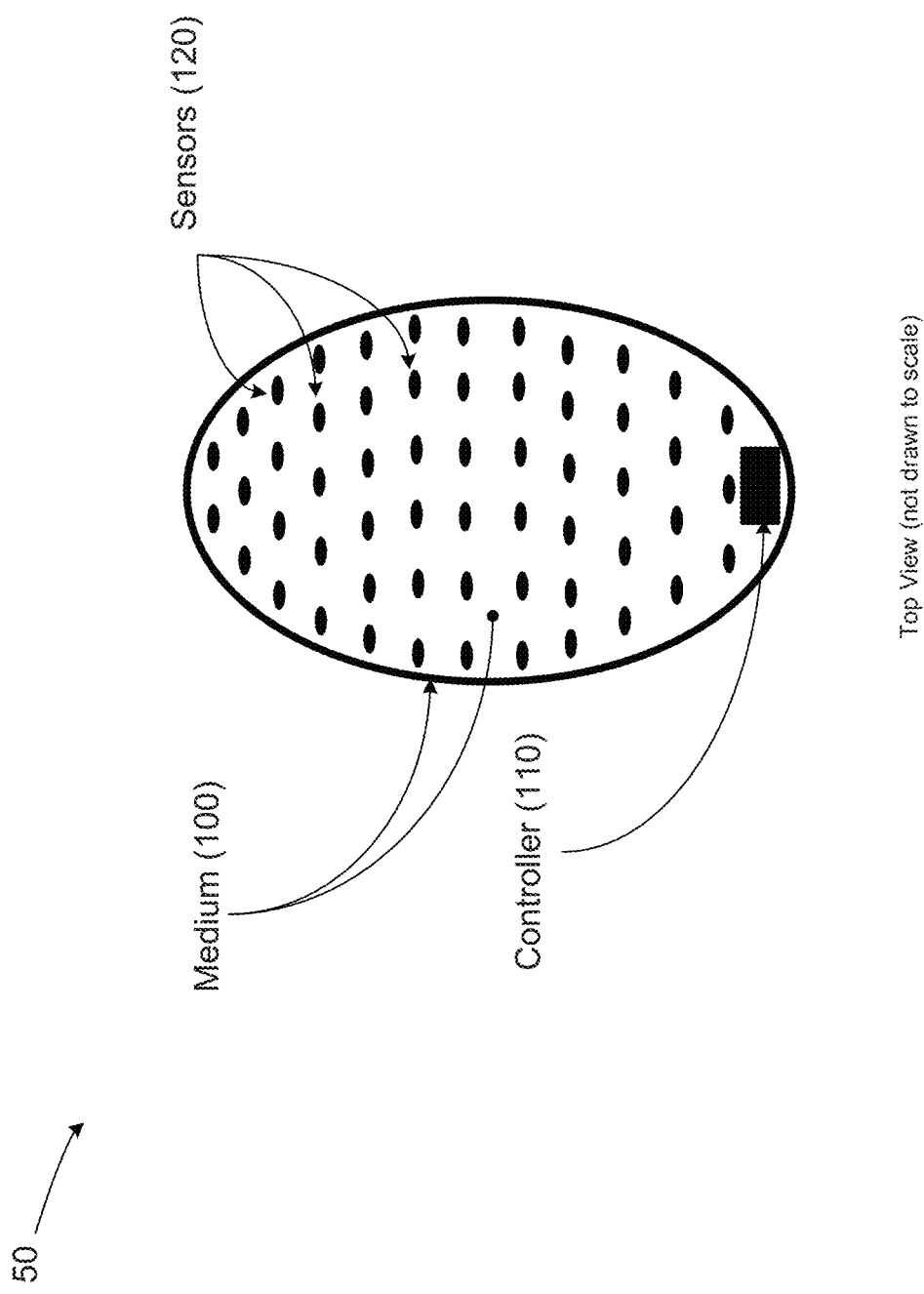
FIG. 2 shows a stylized top view of the sensor arrangement, in accordance with some embodiments.

FIG. 2, illustrates a stylized top view of the sensor arrangement, in accordance with some embodiments. As exemplified in FIG. 2, the sensors 120 are arranged in an exemplary matrix format. However, other sensor arrangements may be used and remain within the spirit and scope of embodiments herein. The sensor arrangement of FIG. 2 may represent a two-dimensional array or matrix of sensors, or in another embodiment, may represent a three-dimensional array or matrix of sensors. The operations of the sensors 120 may be coordinated in some embodiments. For example, the timing of data acquisition using the sensors 120 may be controlled by the controller 110. Further, as a force moves across the array of sensors 120, the controller may use the timing of the sensed data to determine the direction of the movement of the force to determine the direction and/or magnitude of the force sensed by the sensors 120. In one embodiment, a two-dimensional assessment of the force movement or force vector may be made based upon data from the sensors 120. In other embodiments, a three-dimensional assessment of the force movement or force vector may be made based upon data from the sensors 120.

Figure 3:
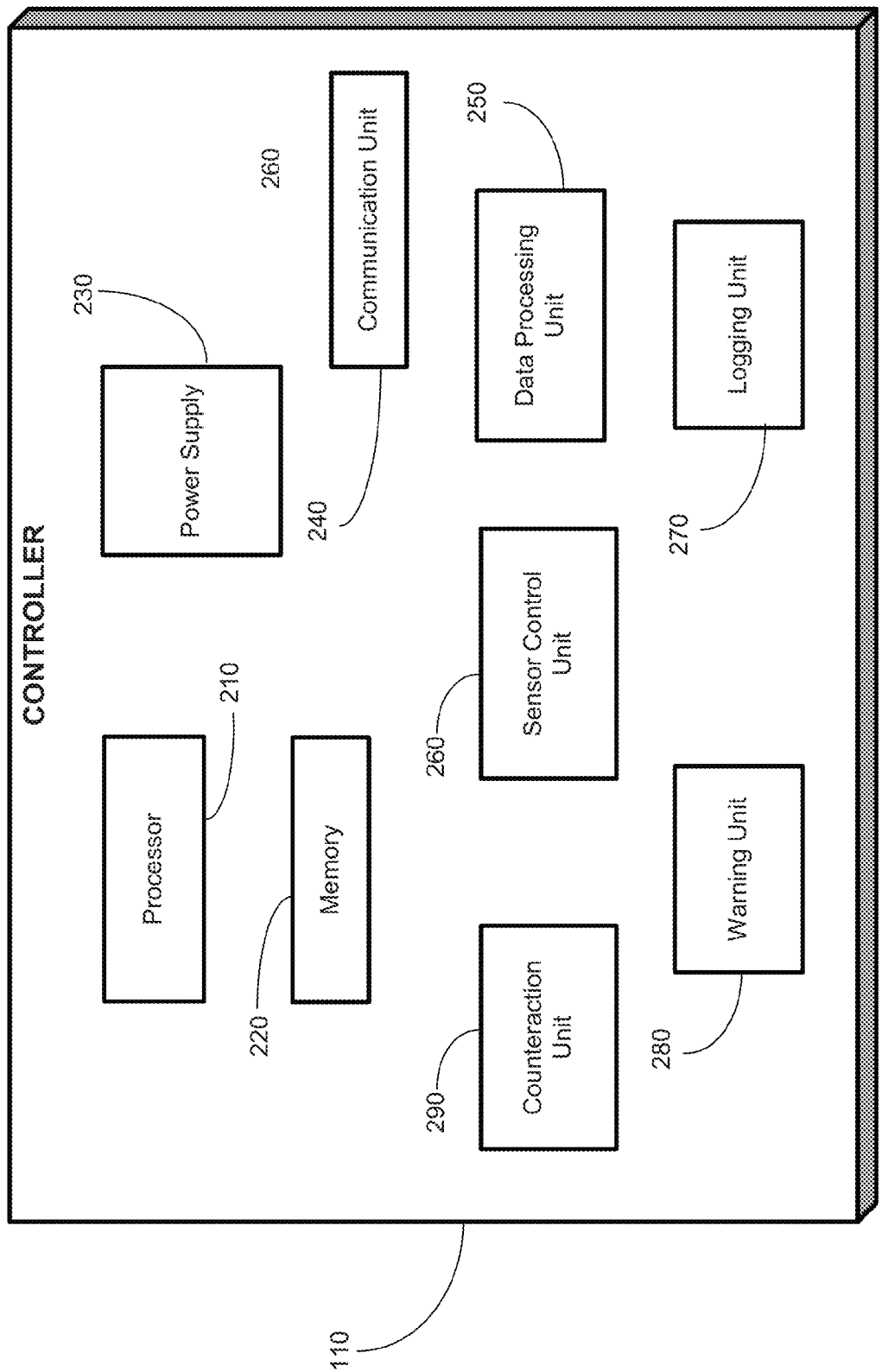
FIG. 3 shows a stylized depiction of a controller of FIG. 1, in accordance with some embodiments.

Turning now to FIG. 3, a stylized block diagram depiction of the controller of FIGS. 1 and 2, in accordance with some embodiments herein, is illustrated. The controller 110 may comprise a processor 210, a power supply 230, a memory 220, a data processing unit 250, a communications unit 240, and a sensor control unit 260. The processor 210 may interface with the memory 220 to perform various lookup functions. The processor 210 may facilitate the communications between the sensors 120 and the controller 110.

The processor 210 may comprise one or more microcontrollers, microprocessors, etc., capable of performing various executions of software and/or firmware components. The memory 220 may comprise various memory portions where a number of types of data (e.g., internal data, external data instructions, software codes, status data, diagnostic data, etc.) may be stored. The memory 220 may comprise one or more of random access memory (RAM), dynamic random access memory (DRAM), electrically erasable programmable read-only memory (EEPROM), flash memory, etc. In one embodiment, a memory 220 may be separate from, but communicatively coupled to the controller 210.

The power supply 230 may provide power for the controller 110 and/or to the sensors 120. In one embodiment, the power supply may be a battery. In other embodiments, power supply 230 may receive power wirelessly, e.g., inductive coupling, capacitive coupling, RF coupling, microwave coupling, etc. The power supply 230 may comprise a power source that in some embodiments may be rechargeable. In other embodiments, a non-rechargeable power source may be used. The power supply 230 provides power for the operation of the medium 100, including electronic operations and the electrical signal generation and delivery functions. The power supply 230 may comprise a lithium/thionyl chloride cell or a lithium/carbon monofluoride (LiCFx), or may comprise conventional watch batteries or 9 Volt batteries. Other battery types known in the art may also be used.

The communications unit 240 provides for communications between the sensors 120 and the controller and/or communication between the controller 110 and an external base unit (e.g., a hand-held device, computer, cellphone, tablet computer, laptop computer, desktop computer, specialized console, etc.).

The controller 110 may also comprise a data processing unit 250. The data processing unit 250 may be adapted to, and/or capable of, collecting data relating to the body of a patient. Such data may be obtained using electrical, chemical, optical, biophotonic, acoustic (e.g., ultrasound), thermal sensors, pressure sensors, bioassays, chemical methods, imaging technology and/or motion sensors in any useful combination (these measurements may be performed at one or multiple spatial scales simultaneously or sequentially (e.g., multiplexing) and include but are not limited to: 1. Neurologic data such as neuronal electrical activity, neurotransmitter concentrations and their rate(s) of release and uptake, Kreb's and other cycle compounds, other chemical compounds (e.g., electrolytes, tissue stress markers), CSF and brain tissue pressure, temperature, and/or kinematic/kinetic activity, including but not limited to posture and fine motor movements among others using imaging techniques (e.g., video), accelerometers, inclinometers, actigraph devices, and/or the like; 1a. Level of consciousness and/or cognitive signals (e.g., attention, reaction time, memory, etc.), neurological tests administered manually and/or automatically for qualitative or quantitative analyses; 2. Cardiac signals (e.g., as discussed above); 3. Body fluids signals including, but not limited to, those that may recorded using pressure, flow velocity and degree of laminarity (or turbulence) (e.g., Doppler), temperature, pH, chemical makeup (e.g., electrolytes, enzymes, tissue stress markers, antioxidants, gases); 4. Respiratory rate, pattern, tidal volume, and/or degree of activity of principal and/or accessory respiratory muscles to compute, for example, ratios (e.g., abdominal wall motion/thoracic wall motion, end tidal $CO_2$); 5. Endocrine indices (e.g., as discussed above); 6. Metabolic parameters (e.g., as discussed above); and 7. Kinetic data (e.g., as discussed above). This list is not exclusive, and the data processing unit 250 may collect additional data not listed herein, that would become apparent to one of skill in the art having the benefit of this disclosure.

The data processing unit 250 may perform various processing of data from the sensors 120. The processing may include buffering, filtering, performing digital signal processing (DSP), calculating force (magnitude and/or direction) detected by the sensors 120. The data processing unit 250 may include various amplifier(s) 320, one or more A/D converters 330 and/or one or more buffers 340 or other memory (not shown). In one embodiment, the amplifier(s) 320 may be adapted to boost and condition incoming and/or outgoing signal strengths for body signals, e.g., from the sensors 120. The A/D converter(s) 330 may be adapted to convert analog input signals from the body data unit(s)/module(s) into a digital signal format for processing by controller 110 (and/or processor 210). A converted signal (e.g., a digital representation of the body signal) may also be stored in one or more buffer(s) 340, a body data memory 350, or some other memory internal to a housing structure capable of housing the medium 100. The buffer(s) 340 may be adapted to buffer and/or store signals received sensors 120.

The controller 110 may also comprise a sensor control unit 260. The sensor control unit 260 may control the operations of the sensors 120. The sensor control unit 260 is adapted to control one or more operations of the sensors 120. The sensor control unit 260 may control the activation, deactivation, on-off timing, etc. of the sensors 120. The sensor control unit 260 may react to prompts from the processor 210, and or from external sources via the communications unit 240.

The controller 110 may also comprise a logging unit 270 that may log various events and their circumstances. For example, if a force above a predetermined threshold is detected by the sensors 120, the details regarding the detected force, the time and date, the environmental conditions, and/or other data may be logged for analysis. Alternatively, such data may be logged as well as transmitted to an external device via the communications unit 240.

The controller 110 may also comprise warning unit 280 capable of providing a warning based upon data from the sensors 120. For example, if a force above a predetermined threshold (e.g., magnitude, direction, time period, etc. of the force) is detected by the sensors 120, a warning may be provided by the warning unit 280. The warning may comprise at least one of a message sent electronically, an audible warning, and a visual warning (e.g., turning on a light, activating an LED, message using an LCD display, etc.).

The controller 110 may also comprise a counteraction unit 290. The counteraction unit 290 may prompt one or more counter action in response to a force above a predetermined threshold is detected by the sensors 120. For example, the counteraction may comprise at least one of deploying a flap from a helmet to counteract the detected force, activating a small air bag device to counteract the force near the location of an impact, activating a mechanical device configures to at least partially counteract the detected force. The counteraction may not only be response to the magnitude of the force, but it may be responsive to the force vector or direction.

In other embodiments, the counteraction unit 290 may be capable of delivering a therapeutic electrical signal to provide a therapy for an injury. For example, if the medium assembly 50 may be capable of determining that an injury has occurred based upon a detected body signal related to a force experienced by a person wearing a housing containing the medium assembly 50. Based upon the determination than an injury has occurred, the medium assembly 50 may deliver an electrical signal to treat the injury. For example, if the medium assembly 50 determines that a concussion has occurred, the medium assembly 50 may provide an electrical signal to a portion of the injured person's head to treat the concussion. The medium assembly 50 may determine the location of the injury based upon the sensor array data and target the delivery of the electrical signal accordingly. In some embodiment, one or more sensors 120 may be electrodes capable of delivering an electrical signal. In other embodiment, one or more sensors 120 may be capable of performing a sensing function as well as an electrode signal delivery function. One or more of the blocks illustrated in the controller 110 of FIG. 3 may include or may be comprised of hardware, software, firmware, or any combination thereof.

Figure 4:
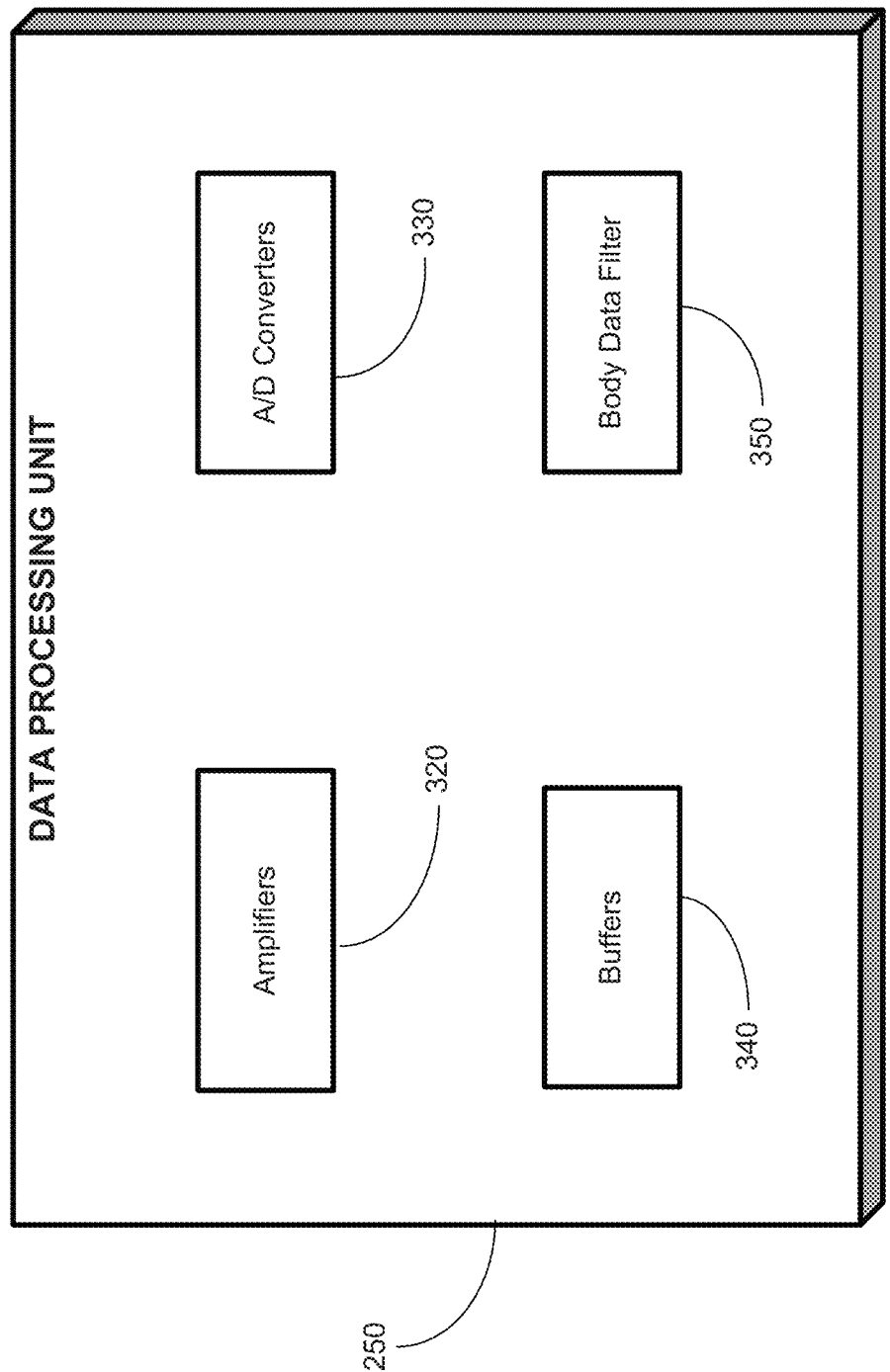
FIG. 4 shows a stylized depiction of the data processing unit of FIG. 3, in accordance with some embodiments.
Figure 5:
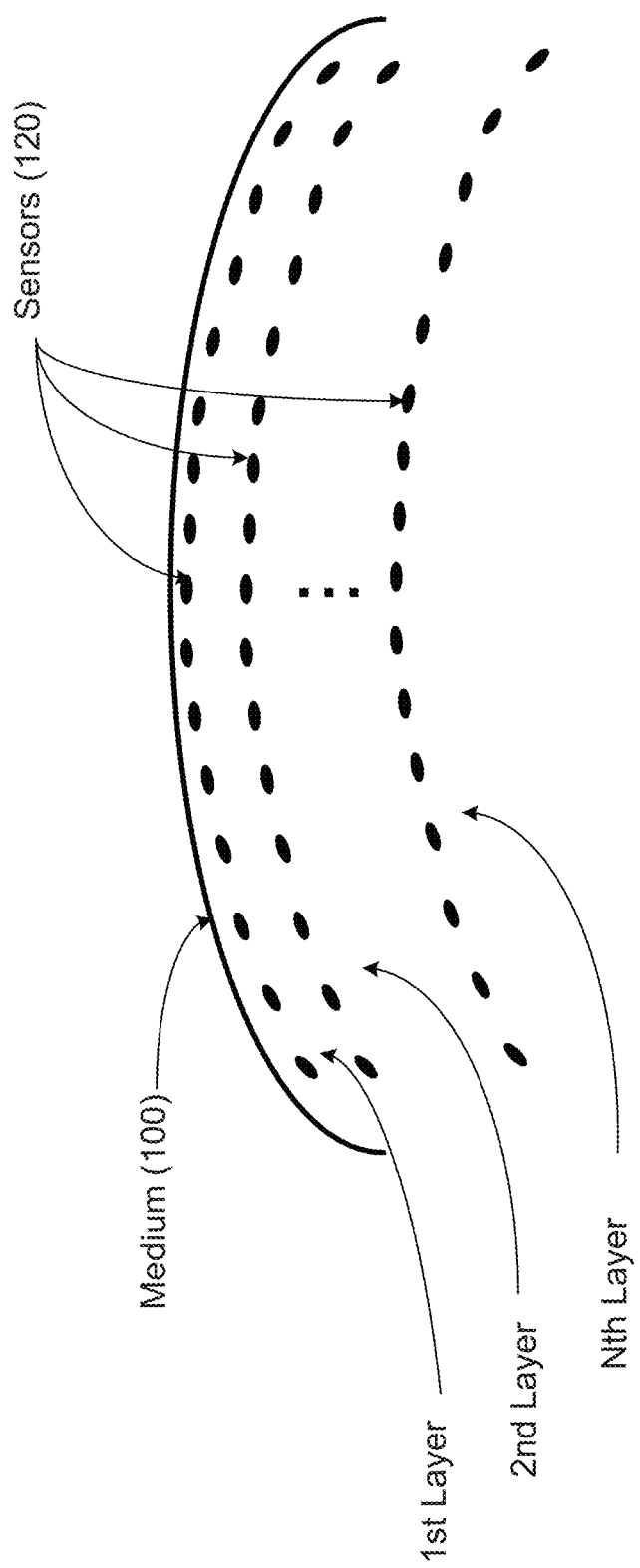
FIG. 5 shows a stylized depiction of another arrangement of sensors, in accordance with some embodiments.

Turning now to FIG. 5, a stylized depiction of another arrangement of sensors, in accordance with some embodiments, is illustrated. As exemplified in FIG. 4, a plurality of layers of sensors 120 may be placed onto the medium 100. The plurality of layers of sensor 120 arranged in a matrix fashion provides for a 3-dimensional matrix of sensors 120. In one embodiment, a first layer of sensors 120 may be arranged above a second layer of sensors 120, which in turn, may be arranged above a third layer of sensors 120, and so on to an $n^{th}$ layer of sensors 120. In one embodiment, the first through $n^{th}$ layer of sensors 120 may be arranged directly above one another. In other embodiments, the first through $n^{th}$ layer of sensors 120 may be arranged such that one or more layers of sensors 120 are offset or staggered relative to other layers of sensors 120. In some embodiments, the medium may be sufficiently thick to house a plurality of sensors layers. In other embodiments, one or more layer below the first layer of sensors may be connected directly to the sensors in the above sensor layers and may not be entirely housed in the medium 100.

Figure 6A:
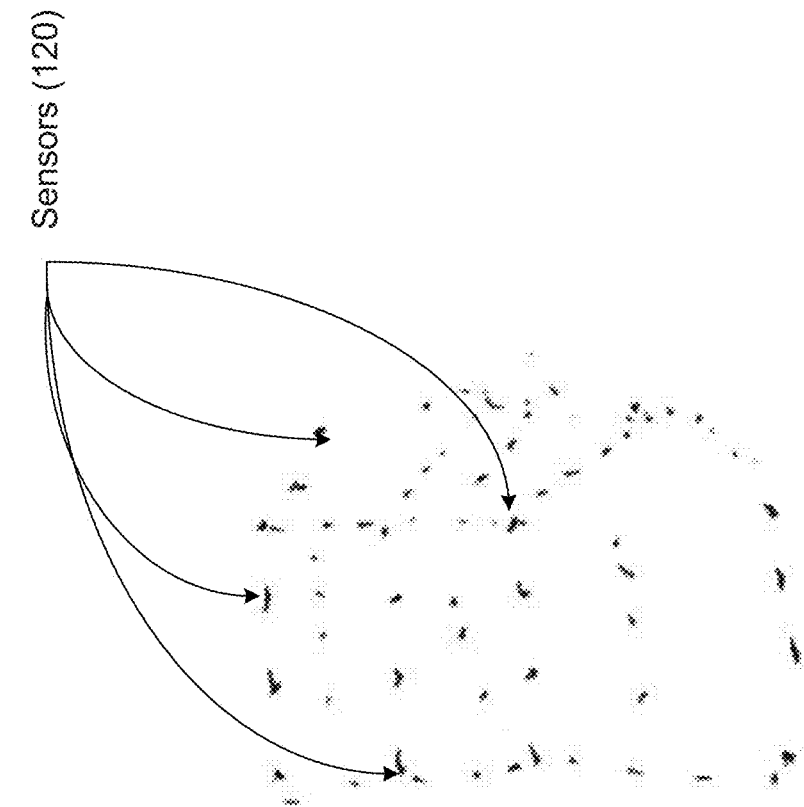
Figure 6A:
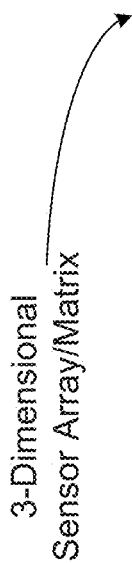

FIGS. 6A and 6B illustrate exemplary configurations for arranging a plurality of sensors in accordance with some embodiments herein. FIGS. 6A and 6B provide exemplary 3-dimensional matrices of sensors 120. FIG. 6A illustrates a first geographical sensor arrangement for providing 3-dimensional indication of a kinetic signal. The arrangement exemplified in FIG. 6A provides for a relatively narrower portion of a matrix near the top and progressively expanding wider near the bottom. This arrangement may be used for a helmet, where the area at the top of the head contains a narrower matrix of sensors/electrodes, while the arrangement expands wider to conform to the geometry of the helmet.

FIG. 6B illustrates a second geographical sensor arrangement for providing 3-dimensional indication of a kinetic signal. In this exemplary arrangement, a more triangular arrangement is provided. One exemplary application of this arrangement is a bicycle helmet arrangement. Those skilled in the art having benefit of the present disclosure would appreciate that other configuration may be made for the sensor arrangement and remain within the spirit and scope of the present invention. Those skilled in the art would appreciate that matrices of other shapes and configuration may also be used while remaining within the spirit and scope of the embodiments disclosed herein.

A force vector resulting from an impact upon the medium assembly 50 may be determined using the 3-dimensional matrices exemplified herein. The kinetic signals sensed by the sensors 120 may be translated into a force vector. The force vector may provide an indication of the angle of incidence, the route of the force vector, the magnitude, etc. of a force experienced by a person wearing a housing (e.g., a helmet) containing the medium assembly 50. In one embodiment, the force vector may comprise at least one of a directional component, a magnitude component, a location component, and/or a durational component.

In some embodiments, the timing differences in the signals sensed by various sensors arranged in a matrix may be used to determine the gradient of the kinetic signal. Further, the location of the sensor(s) that detect the kinetic signal may be used determine the direction of and/or location of the kinetic signal. Moreover, the amount of time in which the sensors detect the kinetic signal above a threshold magnitude may be used to determine time period of a kinetic event, e.g., an impact. In this manner, the direction of a force, the location of the force, and a duration of the force caused by a kinetic event may be determined.

Further, the direction of a force, the location of the force, and the duration of the force caused by a kinetic event may be used to determine a kinetic index, which may provide an indication of the amount of force experienced by a person, and/or the injury sustained by the patient. The kinetic index may be a function of various components of the kinetic signal sensed by the sensors 120, as indicated in Equation-1:

$$K_i = f(D_f, M_f, L_f, T_f);$$  Eq. 1 wherein $K_i$ is the kinetic index, $D_f$ is the direction of the kinetic event or force experienced by the wearer of the medium assembly 50, $M_f$ is the magnitude of the force, $L_f$ is the location of the force upon the person's body at its greatest magnitude, and $T_f$ is the time period of the kinetic event or the duration of the existence of the force. The kinetic index may be used to determine a force gradient or force vector. The force vector may comprise direction information, magnitude information, as well as duration information. The kinetic index and/or the force vector may be used to determine the extent and/or type of an injury sustained by the person wearing a housing (e.g., a helmet) containing the medium assembly 50.

In some embodiments, a look-up function may be performed to determine whether the kinetic index is indicative of an injury. The kinetic index may be compared to a threshold value to determine whether an injury of sufficient magnitude has occurred, e.g., a concussion. The injury may be classified, e.g., minor concussion, medium concussion, severe concussion, etc. The sensors may be triggered to sense additional body signals, e.g., brain waves, cardiac signals, respiratory signals, and perform additional determinations of the category, longevity, classification, and/or severity of the injury. In other embodiments, the additional analysis of body signals may be used as confirmation of the determination of the injury. In some embodiments, the kinetic index and/or other body signals described herein may be used to perform a prediction function for prediction a possible health condition or health risk.

Moreover, additional factors may be used to determine the kinetic index. For example, a weighting function for each of the parameters used in Equation 1 may be applied to determine the kinetic index. For example, a weighting factor may be applied to the duration, location, and/or magnitude of the kinetic signal. In some cases, additional weight may be provided to the location of the kinetic signal, wherein some portion of the brain is more sensitive or susceptible to injuries. In this case, a higher weight to the location of the kinetic signal may be provided. In other example, additional weight to the magnitude of the force, or to the direction of the force, may be applicable to determine the kinetic index. This is exemplified in Equation-2:

$$K_i = f([D_f * W_{Df}], [M_f * W_{mf}], [L_f * W_{Lf}], [T_f * W_{Tf}]);$$  Eq. 2 wherein $W_{Df}$ is the weighting factor applied to the direction of the kinetic event or force, $W_{mf}$ is the weighting factor applied to the magnitude of the force, $W_{Lf}$ is the weighting factor applied to the location of the force upon the person's body at its greatest magnitude, and $W_{Tf}$ is the weighting factor applied to the time period of the kinetic event or the duration of the existence of the force.

In other embodiments, other factors may be applied when determining the kinetic index. For example, other body signals, such as a cardiac index, respiratory index, and/or neurological index may be added when determining the cardiac index, respiratory index, and/or neurological index may be respectively determined using cardiac data (e.g., heart rate data) respiratory data (e.g., respiratory rate data), and/or neurological data (e.g., brain wave data). Some uses of these additional indices are exemplified in Equation-3 though Equation-6:

$$K_i = f[([D_f*W_{Df}], [M_f*W_{mf}], [L_f*W_{Lf}], [T_f*W_{Tf}])]*C_i; \quad \text{Eq. 3}$$

$$K_i = f[([D_f*W_{Df}], [M_f*W_{mf}], [L_f*W_{Lf}], [T_f*W_{Tf}])]*R_i; \quad \text{Eq. 4}$$

$$K_i = f[([D_f*W_{Df}], [M_f*W_{mf}], [L_f*W_{Lf}], [T_f*W_{Tf}])]*N_i; \quad \text{Eq. 5}$$

$$K_i = f[([D_f*W_{Df}], [M_f*W_{mf}], [L_f*W_{Lf}], [T_f*W_{Tf}])]*f[C_i,R_i,N_i]; \quad \text{Eq. 6}$$

wherein $C_i$ is the cardiac index, $R_i$ is the respiratory index, and $N_i$ is the neurological index. As indicated in Equations 3-6, the value of the kinetic index may be affected by the cardiac index, respiratory index, neurological index, and/or a combination of the three indexes. Other body data indices may also be applied to determine the kinetic index. Further a safety index may be determined based upon the kinetic index and/or other body data indices. For example, body temperature, oxygen saturation, body chemistry, etc., may be used to determine the safety index. The responsive action described may be triggered by the kinetic index and/or the safety index. In some embodiment, the sensors may acquire data indicative of the various indexes described above. In alternative indexes, an external device may be used to acquire data indicative of the various indexes described above. For example, an external device comprising one or more sensors worn on the wrist may be used to acquire data indicative of the various indexes described above.

In an alternative embodiment, an additional factors relating to the number of previous force values may be used to determine the kinetic index. For example, the number of previous kinetic indexes above a predetermined threshold may be taken in to account when determining the present kinetic index. In some embodiments, one or more components of the signal(s) sensed by the sensors 120 may be analyzed and compared to a corresponding reference or threshold value. For example, the directional component, the magnitude component, the location component, and/or the duration component of the signal from the sensors 120 may be parsed. These components may then be respectively compare to a corresponding directional threshold, a magnitude threshold, a location threshold, or a duration threshold to determine whether the signal is indicative of a health risk. In some embodiments, the location threshold may include information regarding predetermined location(s) of the brain that are deemed to be more sensitive to injuries resulting from impact force. Similar sensitive locations in other portions of a human body, e.g., portion of a person's knee, etc.) may also be used in determining a location threshold.

Using the number of previous kinetic indexes or events to determine the current kinetic index is exemplified in Equation-7:

$$K_i = f[([D_f*W_{Df}], [M_f*W_{mf}], [L_f*W_{Lf}], [T_f*W_{Tf}])]*NuK_i; \quad \text{Eq. 7}$$

$$NuK_i = \Sigma(K_{1-n}); \quad \text{Eq. 8}$$

wherein $NuK_i$ (i.e., $\Sigma(K_{1-n})$) represents an accumulated number of kinetic indexes or kinetic events (1 through n occurrences) experienced by a person either to date, or within a predetermined time period. As an example, the value of the kinetic index is increased if a person has previously experienced a kinetic event (e.g., a concussion). Additionally or alternatively, if a person has previously experienced a kinetic event the threshold to determine whether a kinetic index is indicative of a health risk may be lowered. Thus, the more kinetic events (e.g., concussions) a person has experienced, the lower the value of the kinetic index that is required to indicate a health risk.

Further, in some embodiments, the time elapsed since the previous kinetic indexes that were above a predetermined threshold may be taken in to account when determining the present kinetic index, as exemplified in Equation-9:

$$K_i = f[([D_f*W_{Df}], [M_f*W_{mf}], [L_f*W_{Lf}], [T_f*W_{Tf}])]*1/E_T; \quad \text{Eq. 9}$$

wherein $E_T$ is the elapsed time that has passed since a previous kinetic event. The elapsed time, $E_T$, may inversely affect the value of the kinetic index. Therefore, the longer the elapsed time, $E_T$, has passed the last kinetic event (e.g., concussion), the lower the kinetic index. Conversely, if the elapsed time since a previous kinetic event is relatively small, then a smaller kinetic index is required to trigger a risk of health warning and/or action. In some embodiments, if the user has not experienced a concussion with a second time window, then a higher threshold may be set for the kinetic index to trigger a determination of an injury of a health risk.

Moreover, the number of previous kinetic events and the time elapsed may be both included in determining the kinetic index. For example, if it determined that a user of the medium assembly 50 has experienced two concussions within a first time window, then a lower threshold may be set for the kinetic index to trigger a determination of an injury of a health risk. The use of the elapsed time and the number of previous kinetic events is exemplified in Equation-10:

$$K_i = f[([D_f*W_{Df}], [M_f*W_{mf}], [L_f*W_{Lf}], [T_f*W_{Tf}])]*1/E_T; \quad \text{Eq. 10}$$

Figure 7:
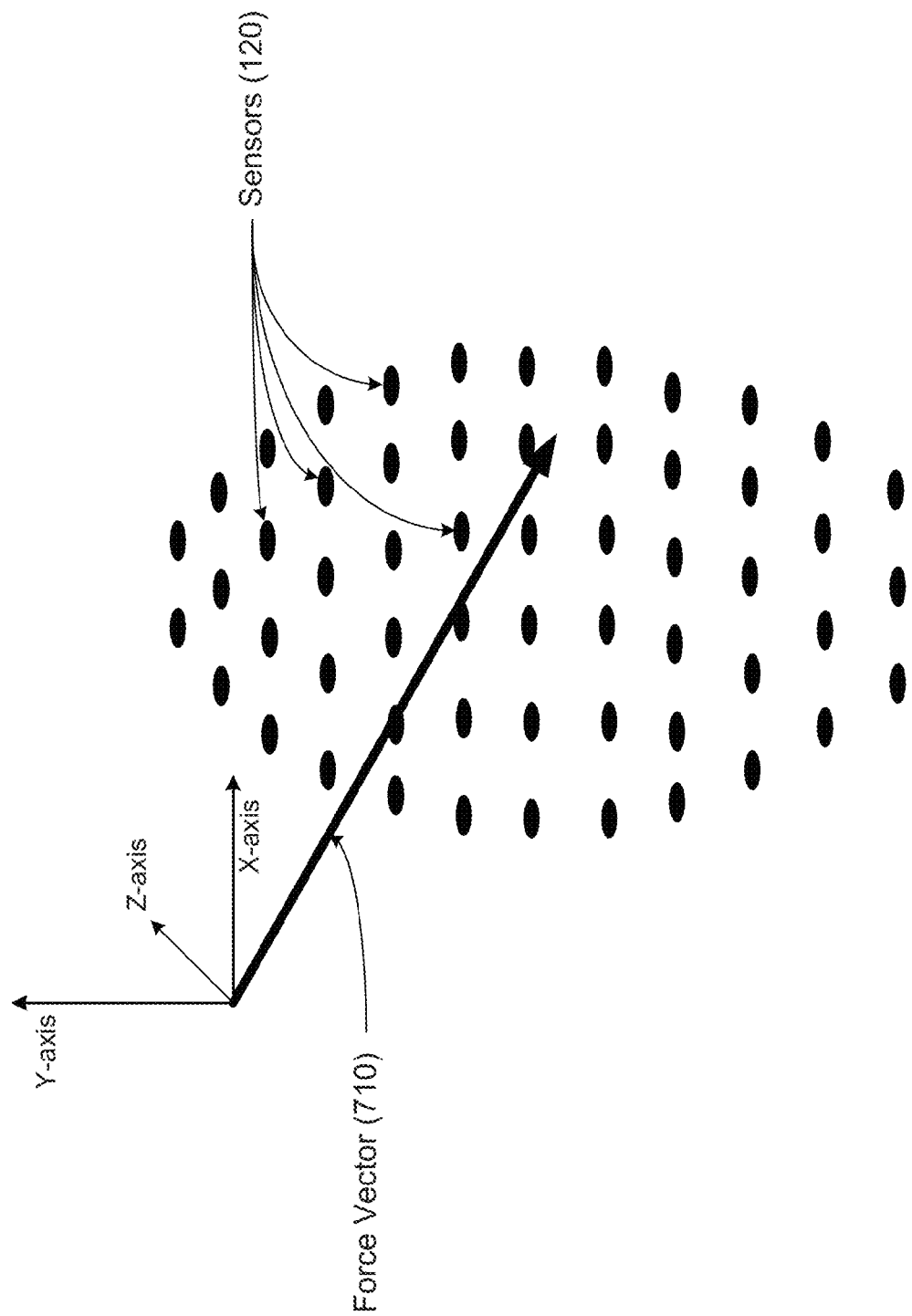
FIG. 7 shows a stylized depiction of a sensor matrix, in accordance with some embodiments.

FIG. 7 illustrates a stylized depiction of a 3-dimensional arrangement of sensors in accordance with some embodiments herein. FIG. 7 illustrates X-Y-Z coordinate in relation to a sensor matrix arranged in a 3-dimensional format. FIG. 7 illustrates a force vector 710 as it travels through the sensor matrix. The force vector 710 may be determined by the controller 110 based upon data from the sensor matrix. In some embodiments, the movement, timing, magnitude, etc. of the force vector may be used to determine the amount of kinetic force experienced by a portion of the user's body wearing the housing containing the sensor matrix. For example, the amount of time the force vector takes to travel from one end of the sensor matrix to the other end may be used to determine amount of kinetic force experienced by a portion of the user's body. The magnitude and direction of the force vector 710 may also be used to determine the amount of kinetic force experienced by a portion of the user's body. The amount of kinetic force experienced by a portion of the user's body may be used to characterize an injury experienced by the user.

Figure 8:
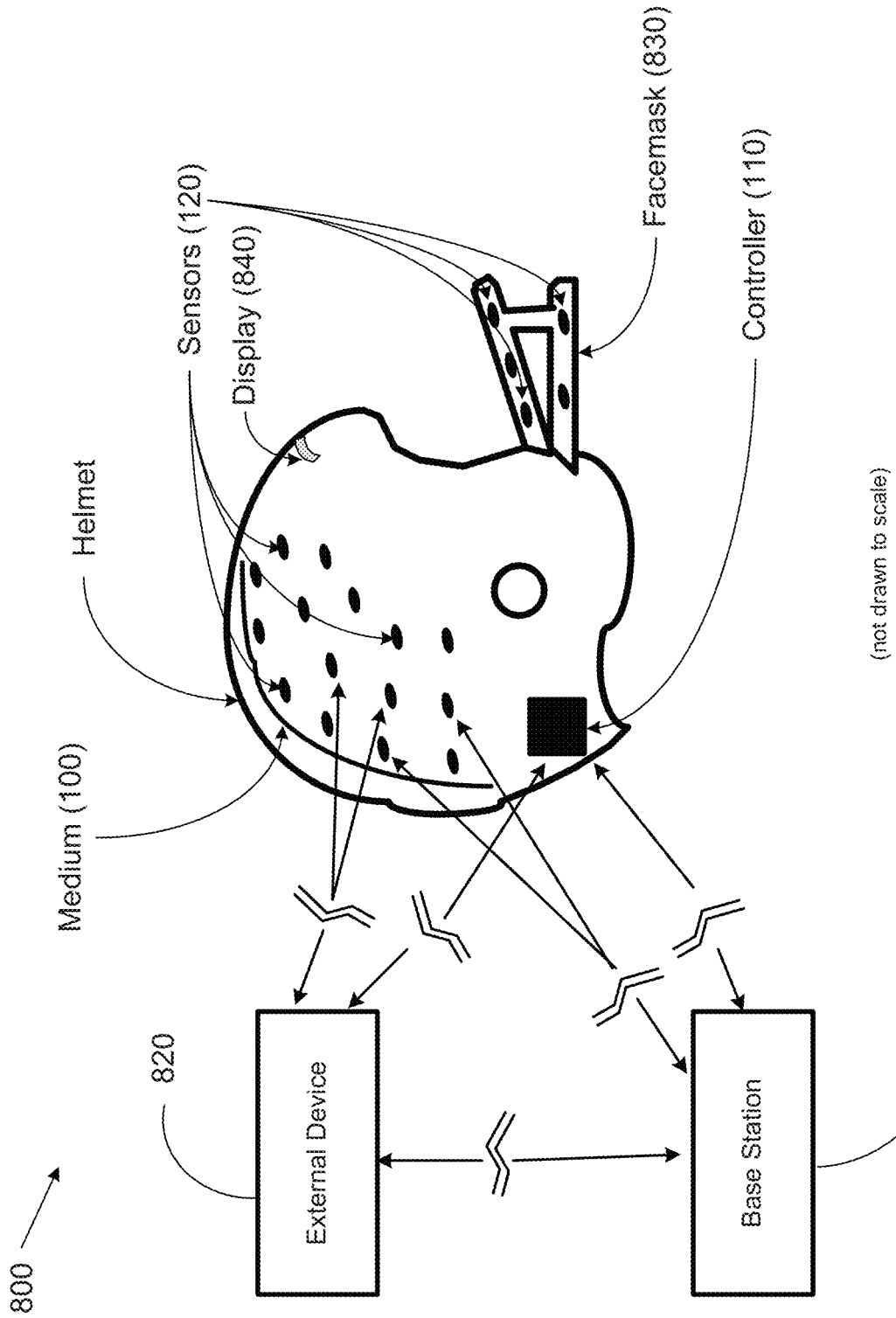
FIG. 8 shows a stylized depiction of a system, in accordance with some embodiments.

FIG. 8 illustrates a system for sensing a kinetic index, in accordance with some embodiments herein. The system 800 includes a housing, such as a helmet, for housing the medium assembly 50, an external device 820, and a base station 810. Referring simultaneously to FIGS. 7 and 8, in one embodiment, the sensors 120 arranged in the medium assembly 50 may be installed into a helmet (e.g., a U.S. football helmet, a hockey helmet, a baseball batter's helmet, a race-car driver's helmet, ski-helmet, a skate-helmet etc.). In one embodiment, a 3-dimensional sensor matrix arrangement may be installed into the helmet. An impact force on the helmet may be detected by the sensor matrix. The direction and the magnitude of the force of the impact may be determined by the helmet comprising sensor matrix. The direction of the force may be defined in terms of a 3-dimensional axis α-axis, y-axis, z-axis), wherein three different angles of the force vector, may be determined.

In one embodiment, a medium assembly 50 comprising the sensor matrix may be installed into a U.S. football helmet, as exemplified in FIG. 8. FIG. 8 shows a system in which a helmet comprising the sensor matrix in communication with a base station. Upon an impact on the helmet, a force vector exemplified in FIG. 7 may appear. In some embodiments, sensors or sensor matrices may be placed in the facemask of the helmet for additional sensing data. The sensor matrix may then determine the three-dimensional definition of the force vector 710. The controller 110 may then be able to determine whether there is a health risk due to the magnitude and/or the direction of the force vector 710.

The health risk may be defined in terms of an injury, a degree of the injury, a risk of health problem, a location of the injury, a probability of an injury, the probably longevity of the injury, etc. A concussion index may be determined based upon the health risk, the kinetic index, and/or the force vector 710. In one embodiment, the concussion index may be based upon the intensity of the injury, the location and/or the spread of the injury, the impact duration, and/or the probably longevity of the injury. The health risk determined by the controller 110 may also be based upon the probability of certain injuries, e.g., probability of concussion, dizziness, brain injury (e.g., traumatic brain injury), internal hemorrhaging, neck injury, vertebrae injury, back injury, heat exhaustion, excessive body temperature, etc.

In one embodiment, information regarding the force vector 710, the kinetic index, the health risk and/or the concussion index may be transmitted from the helmet to a base station 810 (FIG. 7). The base station 810 may be a computer system comprising communications link (e.g., wireless communications) to the helmet. The base station 810 may then compare the magnitude and/or direction of the force vector 710, the kinetic index, the health risk and/or the concussion index to corresponding predetermined reference values, thresholds, and/or reference ranges. The reference values, thresholds, and/or reference ranges may be numeric-based, pattern-based, and/or combination of two.

When the base station 810 determines that the force vector 710, the kinetic index, the health risk and/or the concussion index exceeds corresponding reference values, thresholds, and/or reference ranges, and/or matches a predetermined pattern of magnitude and/or direction, a responsive action is taken. The responsive action may include one or more of providing a warning, logging the event (including details of the force vector, time and date, etc.), switching on an indicator (e.g., an LED) on the helmet, and/or disqualifying the player wearing the helmet from further action, and/or providing a therapy. The warning may be provided on a display 840 affixed to the helmet. The display 840 may be operatively coupled to the controller 110. In some embodiments, the display 840 comprises an LED display and/or an LCD display. The display 840 may provide digital messages and/or color-coded messages, e.g., red for an indication of a health risk, e.g., concussion. One or more of the actions taken by the base station 810 may be performed by the controller 110. In this manner, the location or focus of the injury may be determined, thereby allowing for faster and more accurate assessment of a person's injury. The sensor matrix is capable of pinpointing the focus of the force on a person's body, including the magnitude and direction. Therefore, faster and more accurate assessment of possible concussion may be determined. Further, in some embodiments, the sensor matrix may be formed within knee pads, shoulder pads, wrist supports, etc. Any type of an impact force other types of forces, such as rotational force on the knee, may be detected, assessed, and followed up the a responsive action (treat, log, and/or warn).

Figure 9:
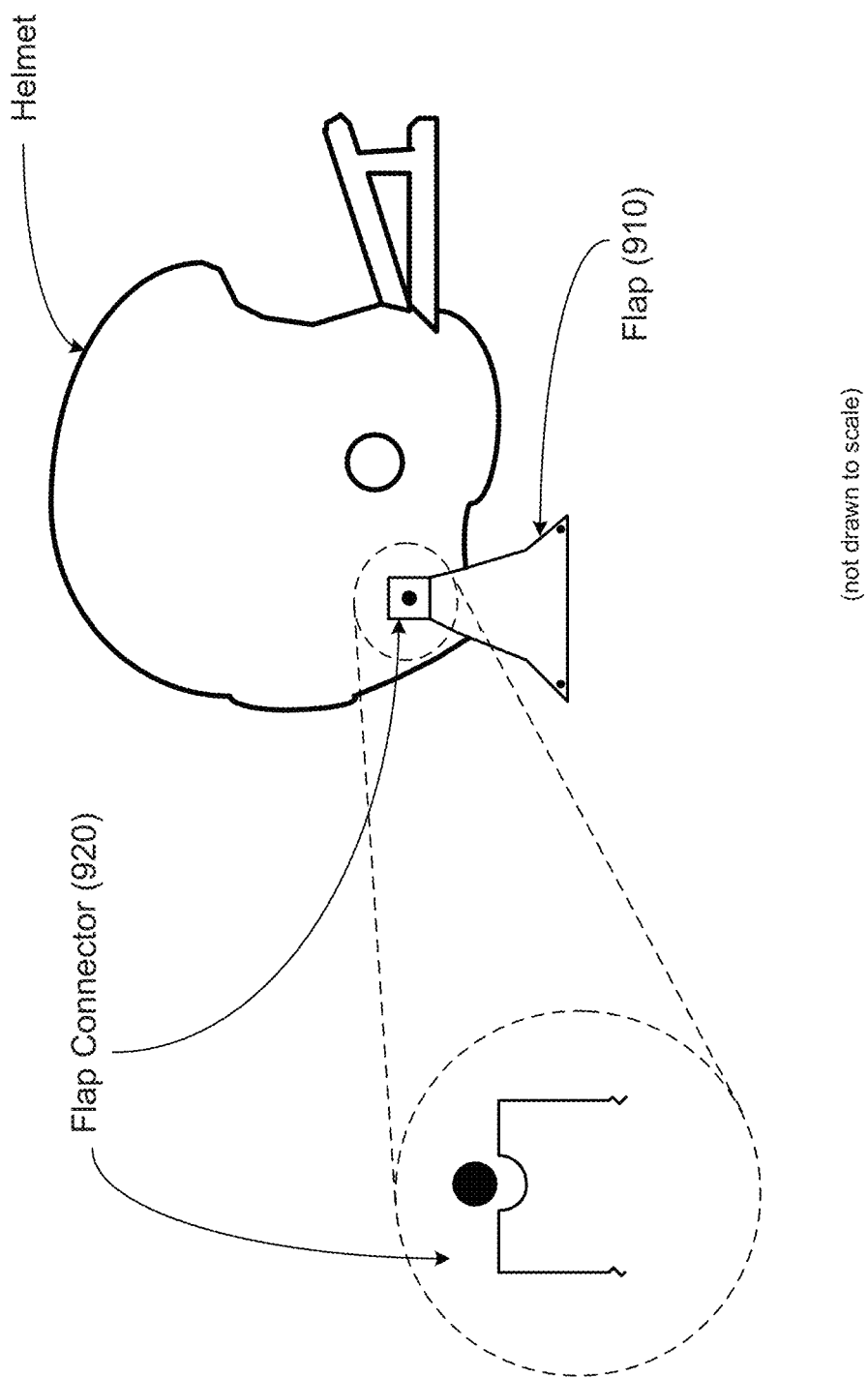
FIG. 9 shows a stylized depiction a helmet, in accordance with some embodiments.

Turning now to FIG. 9, a stylized depiction of a helmet, in accordance with some embodiments is illustrated. FIG. 10 illustrates a more detailed depiction of the helmet prong of FIG. 8, in accordance with some embodiments. Referring simultaneously to FIGS. 9 and 10, in one embodiment, a flap 910 may be coupled to a helmet (e.g. a U.S. football helmet). The coupling of the flap 910 and the helmet may be may be such that a predetermined degree of movement is allowed between the helmet and the flap 910. Therefore, a player would be able to move with a significant degree of freedom. In one embodiment, a sensor matrix described above may be affixed into the helmet of FIG. 9. In some embodiments, sensors or sensor matrix may be placed into the facemask 930. The sensors in the facemask 830 are operatively coupled to the controller 110, the external device 820, the base station 810, and/or to the other sensors in the helmet. Upon detecting an impact force, the flap 910 may become more rigid, such that the freedom of movement of the neck and head of the player may be diminished, thereby reducing the likelihood of a more serious injury.

In one embodiment, upon detection of the impact, the flap mechanism may stiffen to restrict the movement of the head and neck. In an alternative embodiment, the flap connector 910 may be a mechanically driven device. Upon experiencing force, the flap connector 920, which comprises a recess to accommodate the helmet prong 1010, may lock into the helmet prong 1010. This lock action may stiffen the movement of the flap 910, thereby restricting the movement of the neck and head of the player, thereby reducing injury and/or the likelihood of injury. In one embodiment, the distal end of the flap (from the helmet) may be loosely affixed to a shoulder pad of the player, therefore, during normal motion, the player has mobility, but when the flap connector engages (locks with the helmet prong 1010); movement of the neck is restricted to prevent injury. The flap 910 may be positioned strategically to prevent various type of neck movement that could result in injury.

The detection systems described in embodiments described above may be used to not only detect, predict, and/or prevent injuries; they may also be used to test wearable housings (e.g., helmets, apparels, paddings, braces, etc.). Force tests may be performed on wearable housings containing the medium assembly 50 to determine their quality (e.g., injury prevention quality) and/or to improve designs of the wearable housings. For example, tests may be performed on a U.S. football helmet to design and/or improve the concussion resistance offered by the helmet. Based upon tests performed using embodiments described herein, adjustments to the shock absorption with regard to targeted locations on the wearable housings may be made as to increase its resistance to injuries, such as concussions.

Further, the medium assembly 50 may be placed into various wearable housings (e.g., helmets) manufactured by a variety of entities for testing and certification. For example, a safety-related organization may using the medium assembly 50 to certify, classify, and/or rank the safety levels of wearable housing (e.g., helmets) manufactured by a variety of manufacturers. A standard for safety may be established, and the medium assembly 50 may be used to perform tests (e.g., drop tests, impact tests, etc.) in order to certify, classify, and/or rank the wearable housing based on the standards. Based upon these tests, recommendations may be made as to improvements (e.g., stiffer or better protection for a back portion of a helmet, etc.) that can be made to the wearable housings in order to improved safety and functionality.

Those skilled in the art having benefit of the present disclosure would appreciate that the exemplary description provided herein was provided for ease of illustration, and that the concepts disclosed herein may be applied to various contexts. These contexts include, but are not limited to, helmets of various types, e.g., baseball helmets, race-car helmets, bicycle helmets, fire-fighter helmets, work-place helmets (e.g., factory helmets, construction helmets, etc.), military helmets, etc. Further, embodiment herein may be employed in other contexts, such as on clothing (e.g., sports uniforms, police uniforms, fire-fighter uniforms, military uniforms), spacesuits, sport equipment (e.g., shoulder pads, knee pads, elbow pads, etc.).

Portions of the disclosed subject matter and corresponding detailed description are presented in terms of software, or algorithms and symbolic representations of operations on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

Note also that the software implemented aspects of the disclosed subject matter are typically encoded on some form of program storage medium or implemented over some type of transmission medium. The program storage medium may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The disclosed subject matter is not limited by these aspects of any given implementation.

Furthermore, the methods disclosed herein may be governed by instructions that are stored in a non-transitory computer readable storage medium and that are executed by at least one processor of a computer system. Each of the operations of the methods may correspond to instructions stored in a non-transitory computer memory or computer readable storage medium. In various embodiments, the non-transitory computer readable storage medium includes a magnetic or optical disk storage device, solid state storage devices such as Flash memory, or other non-volatile memory device or devices. The computer readable instructions stored on the non-transitory computer readable storage medium may be in source code, assembly language code, object code, or other instruction format that is interpreted and/or executable by one or more processors.

The particular embodiments disclosed above are illustrative only, as the disclosed subject matter may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope of the disclosed subject matter. Accordingly, the protection sought herein is as set forth in the claims below.

What is claimed:

1. A method, comprising:
   detecting, by a sensor array comprising a plurality of accelerometers, a kinetic signal;
   determining a kinetic index based upon said kinetic signal;
   determining whether said kinetic index is indicative of an impact force that is above a predetermined threshold; and
   performing a responsive action in response to determining that said kinetic index is indicative of an impact force that is above said predetermined threshold, wherein said responsive action comprises performing a counteraction, wherein performing said counteraction comprises at least one of:
   providing a therapeutic electrical signal to a portion of a person's body; or
   activating a mechanical unit for counteracting said impact force, wherein said mechanical unit comprises locking of a connector mechanism of a flap for stiffening a movement of said flap.

2. The method of claim 1, wherein determining said kinetic index based upon said kinetic signal comprises determining at least one of a direction of said kinetic signal, a location of a force associated with said kinetic signal, or a time period of a kinetic event associated with said kinetic signal.

3. The method of claim 1, further comprising:
   receiving at least one of cardiac data, neurological data, or respiratory data; and
   wherein determining said kinetic index comprises determining said kinetic index based upon said kinetic signal and at least one of said cardiac data, neurological data, or said respiratory data.

4. The method of claim 1, wherein determining whether said kinetic signal is indicative of said impact force that is above said predetermined threshold comprises determining a force vector based upon at least two of said kinetic signal, said force vector comprising at least one of a directional component, a magnitude component, a location component, or a duration component.

5. The method of claim 1, wherein determining whether said kinetic signal is indicative of said impact force that is above a predetermined threshold comprises determining whether said kinetic signal is indicative of a concussion.

6. The method of claim 1, wherein: said responsive action further comprises at least one of providing a warning or logging data associated with said impact force;
wherein providing said warning comprises at least one of:
providing an auditory warning;
providing a visual warning;
providing a mechanical warning; or
providing an electronic warning.

7. An apparatus, comprising:
a plurality of accelerometers arranged to form a two-dimensional matrix configured to detect a kinetic signal, said plurality of accelerometers being arranged into a wearable housing; and
a controller operatively coupled to said plurality of accelerometers, said controller configured to:
receive a kinetic signal from at least one of said plurality of accelerometers;
determine whether a directional component, a magnitude component, a location component, or a duration component of a force vector based on said kinetic signal respectively exceeds a corresponding directional threshold, a magnitude threshold, a location threshold, or a duration threshold; and
perform a responsive action in response to a determination that at least one of said directional component, said magnitude component, said location component, or said duration component of said kinetic signal exceeds a corresponding directional threshold, magnitude threshold, location threshold, or said duration threshold, wherein said responsive action comprises performing a counteraction, wherein performing said counteraction comprises at least one of:
providing a therapeutic electrical signal to a portion of a person's body; or
locking a connector mechanism of a flap for stiffening a movement of said flap.

8. The apparatus of claim 7, wherein said accelerometers are arranged in a plurality of layers to form a 3-dimensional matrix.

9. The apparatus of claim 7, wherein said accelerometers are kinetic sensors.

10. The apparatus of claim 7, wherein said wearable housing is at least one of a football helmet, a baseball helmet, a race-car helmet, a bicycle helmet, ski-helmet, a skate-helmet, a fire-fighter helmet, work-place helmet, a military helmet, a sports apparel, a police uniform, a fire-fighter uniform, a military uniform, a spacesuit, a shoulder pad, a shoulder brace, a knee pad, a knee brace, an elbow pad, an elbow brace, or a wrist brace.

11. A system comprising, comprising:
a housing comprising:
a plurality of accelerometers configured to detect a signal, said plurality of accelerometers being arranged into said housing;
a controller operatively coupled to said plurality of accelerometers, said controller configured to:
receive a signal from at least one of said plurality of accelerometers;
determine a kinetic index based upon said signal;
determine whether there is a health risk based upon said kinetic index; and
perform a responsive action in response to said health risk, wherein said responsive action comprises performing a counteraction,
wherein performing said counteraction comprises at least one of:
providing a therapeutic electrical signal to a portion of a person's body; or
activating a mechanical unit for counteracting said impact force, wherein said mechanical unit comprises a locking a connector mechanism of a flap for stiffening a movement of said flap, and
a base station operatively coupled to said housing, said base station adapted to at least one of receive said a warning, or log said data associated with said health risk.

12. The system of claim 11, wherein said base station is at least one of a mobile phone, a laptop, a server, a workstation, in communication with said controller.

13. The system of claim 11, wherein said accelerometers are arranged in at least one of a 2-dimensional array or a 3-dimensional array.

14. The system of claim 11, wherein said housing is at least one of a football helmet, a baseball helmet, a race-car helmet, a bicycle helmet, ski-helmet, a skate-helmet, a fire-fighter helmet, a work-place helmet, a military helmet, a sports apparel, a police uniform, a fire-fighter uniform, a military uniform, a spacesuit, a shoulder pad, a shoulder brace, a knee pad, a knee brace, an elbow pad, an elbow brace, or a wrist brace.

15. The system of claim 14, wherein said football helmet comprises a facemask, wherein said facemask comprises at least one sensor for providing an impact signal, wherein said impact signal is used for determining said kinetic index.

16. The system of claim 11, further comprising an external device comprising at least one of a cardiac data sensor, a respiratory data sensor, or a neurological data sensor, said external device operatively coupled with at least one of said housing or said base station.

17. The system of claim 15, wherein said kinetic index is determined based upon said signal and at least one of said cardiac data, a respiratory data, or said neurological data.

18. The system of claim 11, wherein said health risk is at least one of a risk of concussion, risk of dizziness, risk of brain injury, risk of internal hemorrhaging, risk of neck injury, risk of vertebrae injury, or risk of back injury, heat exhaustion and excessive body temperature.

19. The system of claim 11, wherein said controller is further adapted to:
determine a concussion index based upon said signal, said concussion index is based upon at least one of a directional component, a magnitude component, a location component, or a duration component of said signal;
determine whether said concussion index is above a predetermined concussion threshold; and
determine that there exists a health risk in response to determining that said concussion index is above said predetermined concussion threshold.

* * * * *